US 12,118,727 B2

United States Patent
Andersson et al.

(10) Patent No.: US 12,118,727 B2
(45) Date of Patent: Oct. 15, 2024

(54) SYSTEM AND METHOD FOR TRAINING A MACHINE LEARNING MODEL AND FOR PROVIDING AN ESTIMATED INTERIOR IMAGE OF A PATIENT

(71) Applicant: RaySearch Laboratories AB, Stockholm (SE)

(72) Inventors: Sebastian Andersson, Stockholm (SE); Kjell Eriksson, Balsta (SE); Stina Svensson, Stockholm (SE); Ola Weistrand, Huddinge (SE)

(73) Assignee: Raysearch Laboratories AB (publ), Stockholm (SE)

( * ) Notice: Subject to any disclaimer, the term of this patent is extended or adjusted under 35 U.S.C. 154(b) by 365 days.

(21) Appl. No.: 17/596,287

(22) PCT Filed: Jun. 1, 2020

(86) PCT No.: PCT/EP2020/065117
§ 371 (c)(1),
(2) Date: Dec. 7, 2021

(87) PCT Pub. No.: WO2020/249414
PCT Pub. Date: Dec. 17, 2020

(65) Prior Publication Data
US 2022/0230319 A1  Jul. 21, 2022

(30) Foreign Application Priority Data
Jun. 13, 2019 (EP) .................................... 19180030

(51) Int. Cl.
*G06T 7/00* (2017.01)
*G16H 30/40* (2018.01)

(52) U.S. Cl.
CPC ........... *G06T 7/0016* (2013.01); *G16H 30/40* (2018.01); *G06T 2207/10076* (2013.01);
(Continued)

(58) Field of Classification Search
CPC ............... G06T 7/0016; G06T 7/33; G06T 2207/10076; G06T 2207/10081;
(Continued)

(56) References Cited

U.S. PATENT DOCUMENTS

2008/0300502 A1   12/2008  Yang et al.
2017/0178391 A1*  6/2017  Svensson ............... G16H 50/50
(Continued)

FOREIGN PATENT DOCUMENTS

EP   3444776 A1   2/2019
EP   3572822 A1   11/2019
(Continued)

OTHER PUBLICATIONS

Brian Teixeira et al: Generating Synthetic X-ray Images of a Person from the Surface Geometry, arxiv.org, Cornell University Library, 201 Olin Library Cornell University Ithaca, NY 14853, May 14, 2018 (May 14, 2018). pp. 1-9.
(Continued)

*Primary Examiner* — John B Strege
(74) *Attorney, Agent, or Firm* — Noréns Patentbyrå AB

(57) ABSTRACT

A deep learning model may be trained to provide an estimated image of the interior of a patient, based on a number of image sets, each image set comprising an interior image of the interior of a person and a contour image of the person's outer contour at a specific point in time. The model is trained to establish an optimized parametrized conversion function G specifying the correlation between the interior of the person and the persons outer contour based on the image sets. The conversion function G can then be used to provide estimated images of patient's interior based on their contours.

15 Claims, 2 Drawing Sheets

(52) U.S. Cl.
CPC ............... *G06T 2207/10081* (2013.01); *G06T 2207/10088* (2013.01); *G06T 2207/20081* (2013.01); *G06T 2207/20084* (2013.01); *G06T 2207/30004* (2013.01)

(58) Field of Classification Search
CPC ... G06T 2207/1088; G06T 2207/20081; G06T 2207/20084; G06T 2207/30004; G06T 2207/30096; G16H 30/40; G16H 30/00; G16H 50/70; G06N 3/044; G06N 3/045; G06N 3/08
See application file for complete search history.

(56) References Cited

U.S. PATENT DOCUMENTS

| | | |
|---|---|---|
| 2018/0228460 A1 | 8/2018 | Singh et al. |
| 2019/0057521 A1* | 2/2019 | Teixeira ............... A61B 90/361 |
| 2021/0220671 A1 | 7/2021 | Erkisson |

FOREIGN PATENT DOCUMENTS

| | | |
|---|---|---|
| JP | 2018535732 A | 12/2018 |
| JP | 2019061710 A | 4/2019 |
| JP | 2020505672 A | 2/2020 |
| WO | 2017141958 A1 | 8/2017 |
| WO | 2017191847 A1 | 11/2017 |
| WO | 2018130890 A1 | 7/2018 |

OTHER PUBLICATIONS

International Search Report. International application No. PCT/EP2020/065117. Patent Cooperation Treaty. European Patent Office, P.B. 5818 Patentlaan 2, NL—2280 HV Rijswijk. Date of mailing of the international search report: Aug. 18, 2020. pp. 1-4.

Jelmer M. Woltering et al: "Deep MR to CT Synthesis using Unpaird Data" Aug. 3, 2017 (Aug. 3, 2017). Retrieved from the Internet: URL:https://pdfs.semanticscholar.org/52fc/fc6b725220baf18cd9c70ca4ea4a3a264cca.pdf [retrieved on Sep. 25, 2018]. pp. 1-12.

Written Opinion of the International Searching Authority. International application No. PCT/EP2020!065117. Filing date: Jun. 1, 2020. Patent Cooperation Treaty. European Patent Office, D-80298 Munich. Aug. 18, 2020. pp. 1-12.

Office Action in corresponding Japanese Application No. 2021-571708, dated May 25, 2024, Japan Patent Office (JPO), Japan.

* cited by examiner

SYSTEM AND METHOD FOR TRAINING A MACHINE LEARNING MODEL AND FOR PROVIDING AN ESTIMATED INTERIOR IMAGE OF A PATIENT

TECHNICAL FIELD

The present invention relates to a method, a computer program product and a computer system for providing an estimated image of a patient for use in medical applications.

BACKGROUND

In radiotherapy, the patient receiving the treatment is normally positioned on a couch, but may also be standing or seated on a chair. The interior of the patient may move because of factors such as respiration, coughing or movement due to discomfort. Such movement may cause the radiation to miss the target and instead hit another organ, possibly an organ at risk. This may cause underdosage to the target and/or overdosage to other tissues or organs, both of which are undesirable and possibly harmful. This problem has been addressed in a number of different ways.

Various attempts have been made at preventing such movement. For example, a patient's possibility to move during treatment may be restricted. In particular, a patient may be instructed to hold their breath, or physically forced to move only within certain limits. This causes discomfort and is only possible to a certain degree and/or for limited amounts of time.

Other attempts of handling this have involved robust planning, in which uncertainties in the positions of various critical organs have been taken into account. This may lead to plans that are not optimal because they have to fit a number of different possible scenarios.

Different methods for target tracking have also been proposed. In European Patent Application No. 18180987 a method is proposed involving imaging of the patient during different phases of the breathing cycle and planning the total dose as a sum of phase doses taking into account the different positions of the target and other organs in the different phases. This requires a number of 3D images, typically CT images of the patient being taken throughout the treatment, leading to considerable additional radiation to the patient, which is undesirable. One alternative is to use MR imaging instead. This involves no radiation but is much slower than CT imaging and/or does not give the same image quality. Target tracking radioactive markers has also been suggested. This only enables tracking of the target, whereas changes in the positions of other organs will not be detected.

SUMMARY

It is an object of the present invention to take into account the periodical or accidental movement of a patient, during a treatment fraction, in radiotherapy treatment planning.

This object is achieved according to the present invention by a computer-based method of training a deep learning model for providing an estimated image of the interior of a patient, based on a number of image sets, each image set comprising a first interior image of the interior of a person and a contour image of the person's outer contour at a specific point in time, and a second interior image of the interior of the person, comprising the steps of a. submitting the image sets to a deep learning model arranged to output an estimated image based on the contour image and the second interior image b. training the model to establish an optimized parametrized conversion function G specifying the correlation between the interior of the person and the person's outer contour based on the image sets by, for at least one image set, applying the model to the contour image and the second interior image of the image set, comparing the output to the first interior image and using the result of the comparison to train the model.

The invention also relates to a method of providing an estimated image of the interior of a patient at a first point in time, comprising the steps of providing an interior image of the interior of the patient at a second point in time, preceding the first point in time, to a deep learning model comprising an optimized parametrized conversion function based on the correlations between contours and interiors of persons, providing a contour image of the contour of the patient at the first point in time to the deep learning model outputting from the deep learning model an estimated image of the patient based on the interior image, the contour image and the optimized parametrized conversion function G.

The methods according to the invention are based on the fact that there is in many cases a correlation between the external contour of a patient and the internal structure, including positions of one or more internal structures such as organs or tissues. The image or images used to provide interior data is typically one or more images taken of the patient in the course of treatment planning and treatment, such as one or more fraction images and/or a planning image. In the method of training the deep learning model, preferably the steps are repeated for all of the image sets. Each contour image may be based on the same image as the corresponding interior image, for example a CT scan of the patient. Alternatively, the contour image may be based on separate image data, for example based on data obtained from a surface scanning device. Typically, the estimated image is used for planning a medical procedure that requires information about the patient's interior, for example a radiotherapy treatment plan, or for modifying an existing plan. If the surface scanning is performed repeatedly, the contour data from subsequent surface scans can be used to produce a 4D image consisting of a series of 3D images corresponding to different points in time. In some embodiments the first interior image and the contour image of each image set are 4D images and the model is trained to output a synthetic 4D image.

The first interior image, taken at substantially the same time as the contour image, serves as the target for what the output from the model should be when based on the contour image and the second interior image. Therefore, the training is based on comparison of the output from the model, that is, the first estimated image, and the first interior image. The second interior image may be an image taken at an earlier point in time, such as a planning image, or a fraction image, of the patient, or may be an estimated image from a previous step in the training model. It is advantageous for the second interior image to be taken close in time to the contour image, for example, a fraction image taken before the same fraction as the contour image, or the estimated image resulting from the immediately preceding step in the training model.

In the method of providing an estimated image, the contour image is preferably based on data obtained from a surface scanning device. Such surface scanning devices are often available in hospitals, for example in radiotherapy delivery systems, for other purposes, such as ensuring correct positioning of patients for each treatment fraction. Therefore, the surface scanning data may often be obtained without the need for additional equipment. Also, the surface scanning data may be obtained without exposing the patient to additional dose.

It follows that the invention enables the provision of one or more estimated internal images of a patient, which will reduce the need for obtaining actual images of the patient, for example for updating a treatment plan after a certain number of treatment fractions. The invention makes it possible to estimate the delivered dose to the patient during each fraction without obtaining a new image of the patient. This will reduce the need to expose the patient to radiation in order to obtain images at different points in time. It will also be useful in situations where further imaging would cause discomfort to the patient.

Machine learning systems are available which, based on large sets of data, can determine correlations between different types of data and use these correlations to process input data. According to the present invention, correlations between a person's external contour and the interior, in particular the positions of organs or other targets within the patient, can be determined based on previous sets of data in which the contour and the interior are both known. The correlation is expressed in the form of a parametrized conversion function G arranged to convert a contour image into an estimated image of the interior of the patient.

In a preferred embodiment of the training method, the training step comprises
  obtaining an initial parametrized conversion function G arranged to convert a contour image into an estimated image of the interior of the patient based on a first image set of the number of image sets;
  obtaining a first estimated interior image by applying the parametrized conversion function G to the contour image and the second interior image of the first image set
  comparing, in a first comparing step, the first estimated interior image to the interior image of the first image pair,
  and adjusting the initial parametrized conversion function G based on the comparison, to form a first parametrized conversion function G1.

In this case, the training step may further comprise:
applying the first parametrized conversion function G1 to the contour image of the second image set to obtain a second estimated image;
  comparing the second estimated image to the interior image of the second image pair, and adjust the initial parametrized conversion function G to form a second parametrized conversion function G2.

Typically, a sequence of such training steps are performed. The initial parametrized conversion function G may be adjusted for each training step, or may be adjusted after a number of training steps.

In the latter case, the training step may further comprise:
  obtaining a second estimated interior image by applying the parametrized conversion function G to the contour image of the second image set
  comparing, in a second comparing step, the second estimated interior image to the interior image of the second image pair,
  and adjusting the initial parametrized conversion function G based on the first and the second comparing step, to form a first parametrized conversion function G1

The first and second interior image of each image set may be segmentation maps, in which case the model is trained to output a segmentation map. The estimated image will then also be a segmentation map. Alternatively, the interior images of each image set may be an image such as a CT or MR image and the model is trained to output a synthetic CT image or a synthetic MR image, respectively, as the estimated image. In other words, the model is normally trained to output a synthetic image of the same modality, format and level of detail as the interior image. Of course, additional conversion steps may be added to obtain an image of another modality or format.

In addition to the interior image and the contour image, each image set may also comprise at least one slice of an MR image to provide additional information about the patient's interior.

The invention also relates to a computer program product which, when executed in a processor in a computer, is arranged to cause the computer to perform the method according to any one of the preceding claims. The computer program product may be stored on a storage means, such as a non-transitory storage means.

The invention also relates to a computer system comprising a processor, and a program memory, said program memory comprising a computer program product according to the above.

BRIEF DESCRIPTION OF THE DRAWINGS

The invention will be described in more detail in the following, by way of example and with reference to the appended drawings, in which.

DETAILED DESCRIPTION

Figure 1:
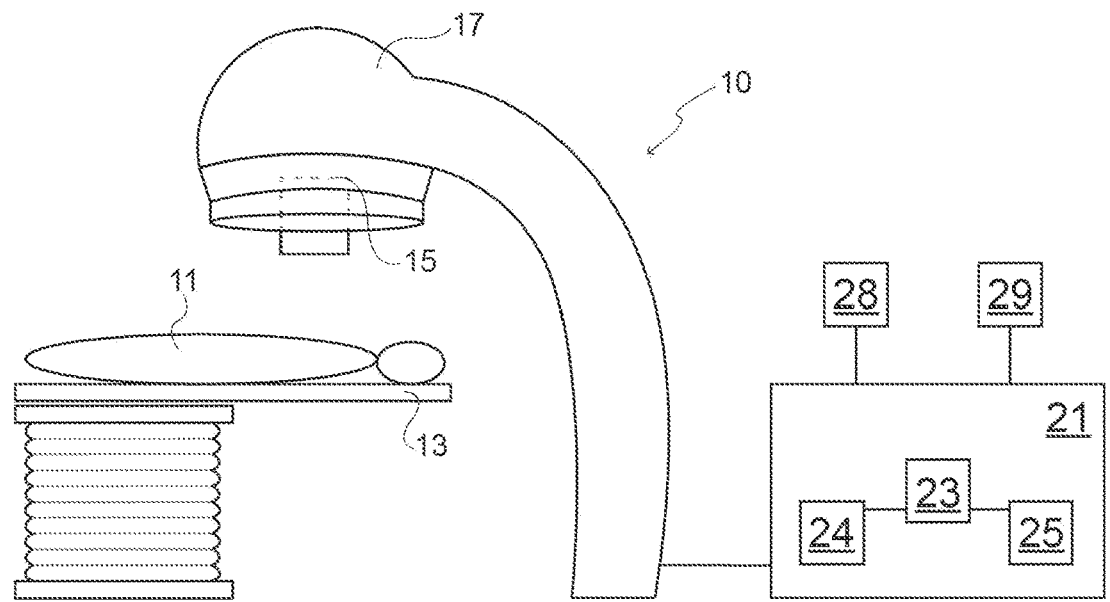
FIG. 1 is a illustrates an imaging system that may be used for the present invention

FIG. 1 is an overview of a system 10 for radiotherapy treatment and/or treatment planning. As will be understood, such systems may be designed in any suitable way and the design shown in FIG. 7 is only an example. A patient 1 is positioned on a treatment couch 3. The system comprises an imaging/treatment unit having a radiation source 5 mounted in a gantry 7 for emitting radiation towards the patient positioned on the couch 3. Typically, the couch 3 and the gantry 7 are movable in several dimensions relative to each other, to provide radiation to the patient as flexibly and correctly as possible. These parts and their functions are well known to the skilled person. A number of devices provided to shape the beam laterally and in depth are typically present and will be not be discussed in more detail here. The system also comprises a computer 21 which may be used for radiotherapy treatment planning and/or for controlling radiotherapy treatment. As will be understood, the computer 21 may be a separate unit not connected to the imaging/treatment unit.

The computer 21 comprises a processor 23, a data memory 24, and a program memory 25. Preferably, one or more user input means 28, 29 are also present, in the form of a keyboard, a mouse, a joystick, voice recognition means or any other available user input means. The user input means may also be arranged to receive data from an external memory unit.

When the system is used for planning, the data memory 24 comprises clinical data and/or other information used to obtain a treatment plan. Typically, the data memory 24 comprises one or more patient images to be used in treatment planning. For training purposes, the data memory holds training sets of input data as will be discussed in more detail below. Each set of input data comprises an image of the contour of at least a part of a patient and an interior image of the interior of the contour, taken at approximately the same time, and possibly other data that may assist in the training. For the purpose of generating estimated interior images, the data memory comprises at least an initial interior image of the patient and a contour image of the patient taken at a different time than the interior image. The program memory 25 holds at least one computer program arranged to cause the processor to perform a method according to FIG. 3 or 4. The program memory 25 also holds a computer program arranged to make the computer perform the method steps discussed in connection with FIG. 3 or 4 to make the computer control the radiotherapy treatment of a patient.

The estimated images may comprise different levels of detail depending on the detail of the interior images used in the training sets. It may be a segmented image, simply showing the position and shape of one or more organs or structures within the patient, or it may have a level of detail comparable to a CT image.

As will be understood, the data memory 24 and the program memory 25 are shown and discussed only schematically. There may be several data memory units, each holding one or more different types of data, or one data memory holding all data in a suitably structured way, and the same holds for the program memories. One or more memories may also be stored on other computers. For example, the computer may be arranged to perform only one of the methods, there being another computer for performing the optimization.

Figure 2:
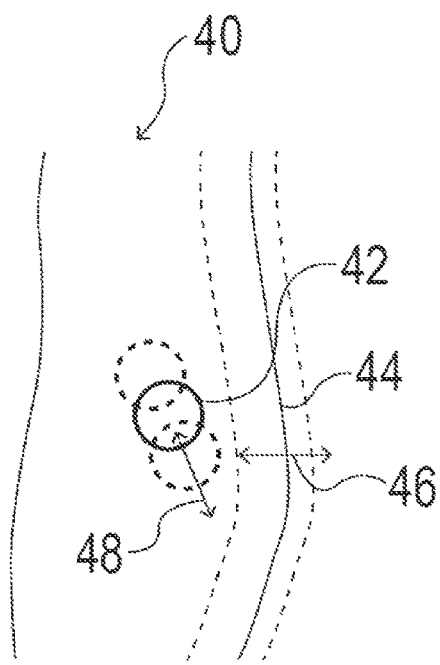
FIG. 2 illustrates the movement of a patient's contour and corresponding movement of an internal organ within the patient.

FIG. 2 shows a part of the torso 40 of a patient, to illustrate a possible correlation between movement of the patient over a breathing cycle and the position of a structure 42, such as a tumor, or an organ at risk within the patient. A first position of the structure 42 is indicated by a solid line. As the patient breathes in and out, the outer contour 44 of the front of the patient will move outwards and inwards, indicated by a first arrow 46. At the same time, the structure 42 will move in a different direction from the contour, typically downwards and outwards, as indicated by a second arrow 48. Examples of the contours, and of the changing positions of the structure are shown as dashed lines.

Figure 3:
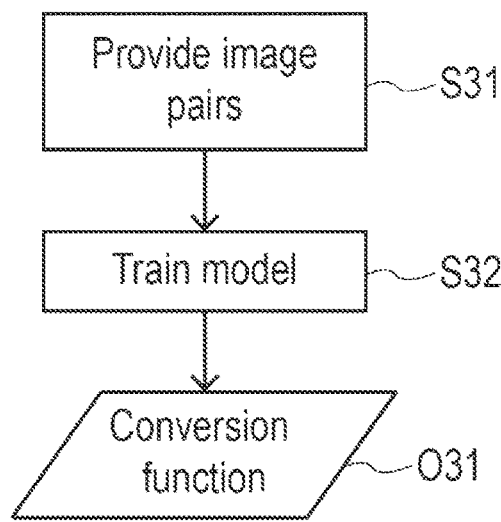
FIG. 3 is a flow chart of a method for training a deep learning model to be used according to the invention

According to the invention, machine learning is used to train a deep learning model using 4D images and corresponding surface contours. In a preferred embodiment the 4D images are CT images but they may be acquired using any suitable imaging technique, including MRI. Input data are preferably pairs of images, a first surface image and a first CT image taken at a first point in time T0 and a second surface image and a second CT image taken at a second point in time T1 and so on. An example of such a training method is shown in FIG. 3.

In a first step S31, a number of pairs of images are provided, each pair consisting of one surface contour of a person and one 3D interior image of the interior of the person, taken at essentially the same time. As discussed above, the interior images may comprise a level of detail depending on the desired level of detail of the resulting estimated images, from a segmented image to a complete CT image. The surface contours may be provided from a surface scanner available near the imaging apparatus or the contour data used for training may be obtained from the 3D images. In a second step S32, the image pairs are used for machine learning to establish a relationship between the surface contour and the position of at least one region of interest in the interior of the person. As is common in the art, this involves generating an optimized parametrized function for converting an image of the surface contour to an estimated image of the interior inside of the contour. Generally, this is achieved by submitting a first surface image to a function, normally together with an earlier interior image of the patient, possibly other image data and a set of activation data. The output from the function is compared to the first CT image taken at the same time as the first surface image. The result of the comparison is used to refine the function. Instead of refining the function after each training step, the function may be refined after a certain number of steps, or only at the end of the procedure. Next, the second surface image is submitted and the function, possibly refined, together with the earlier interior image used above, or another earlier interior image, and the set of activation data, are used to provide second output data. The second output data are compared to the second CT image and the result from this comparison is used to refine the function and the set of activation data again. This is repeated for a number of sets of surface image and CT image. The result of this procedure is a function O31 that may be used to convert contour data of a patient into estimated images of the interior of the patient within the contour.

Preferably, a recurrent, convolutional neural network (RCNN) is used. An RCNN considers information from preceding steps and thereby provides information about the surface or image at a previous point in time. A function correlating the images in a pair obtained at the same time is established and may be used in subsequent procedures to create estimated or synthetic images of other patients.

Figure 4:
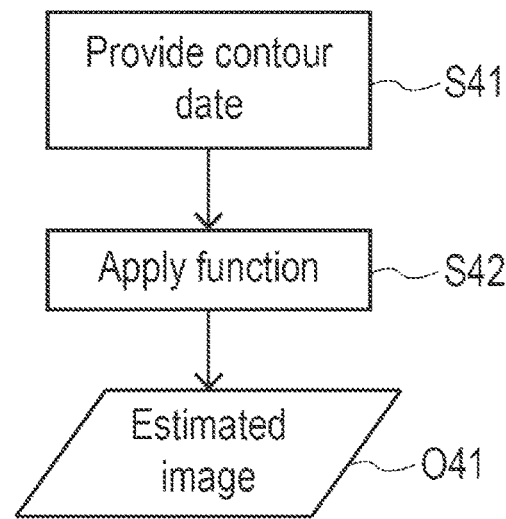
FIG. 4 is a flow chart of a method for using the deep learning model obtained according to the method of FIG. 3 for creating an estimated image of a patient.

When a deep learning model has been trained, that is, the optimized parametrized function has been generated, knowledge about the changes to a patient's contour can be used to determine the position of internal organs within the patient. Input data to this procedure are information related to the surface contour of the patient and an interior image, typically a fraction image. In particular, surface data from different points in time may be used as input data, to return estimated or synthetic images of the patient at the different points in time. The estimated images are created based on the function established in FIG. 3, correlating the contours with the interior CT images as defined in the deep learning model. FIG. 4 accordingly has a first step S41 in which contour data from a patient is provided to a model such as the one created in FIG. 3 and a second step S42 in which an estimated or synthetic image of the interior of the patient based on the contour is created using the function established in step S32.

Figure 5:
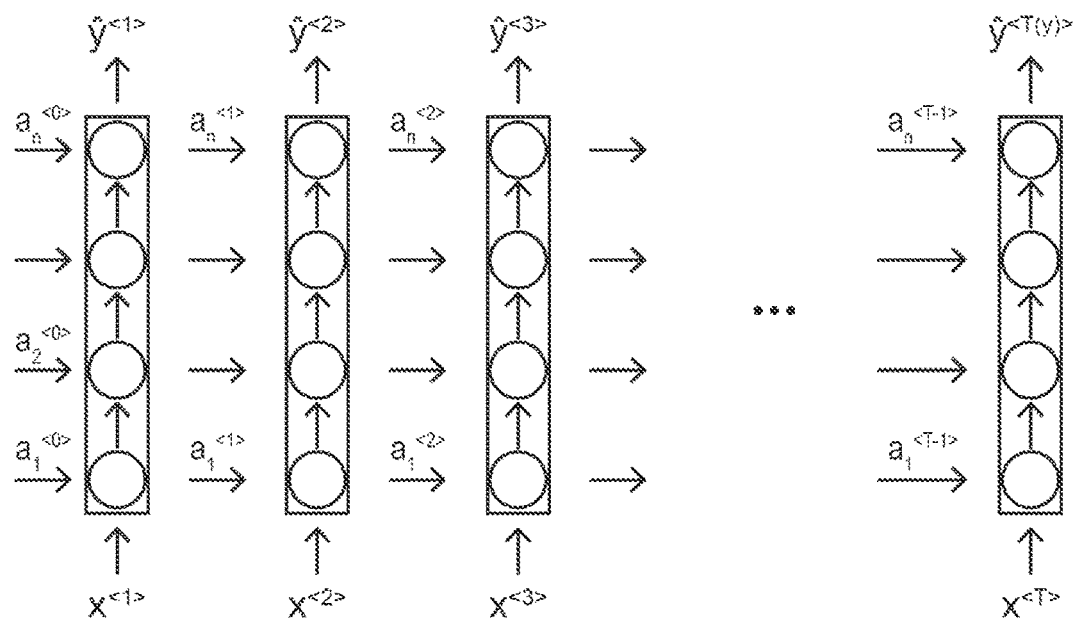
FIG. 5 illustrates a model for machine learning that may be used according to the invention

Any type of recurrent neural network architecture may be used. Common for all recurrent neural networks is that information from an earlier point in time is incorporated in the model. In FIG. 5 a basic example of recurrent neural network is illustrated. As is common in the art, the model is arranged to use a sequence of input data $x^{<t>}$ to the parametrized functions, each represented by the rectangles. The execution of each function is known as a step. Each circle within the rectangles represents a part, also known as layers, of the optimized parametrized function, including weights and operations. The model can be used to produce a set of output data ŷ<t> based on the input data and an activation data vector a<t>. In each case, the label <t> denotes the point in time to which the data relate. So, for example x<1> comprises the patient image taken initially, that is, at t=0, and the contour image taken at t=1. Similarly, ŷ<1> is the estimated image of the internal of the patient at t=1, based on input data x<1> and activation data a<0>, which, as is known in the art, may be a zero vector but may also be a suitable set of input activation data. As is known in the art, the equations related to the basic recurrent convolutional neural network, where * denotes convolution are:

$$a_0^{<t>} = g_0(W_{a0}*a_0^{<t-1>} + W_{x0}*x^{<t>} + b_{a0})$$

$$a_1^{<t>} = g_1(W_{a0}*a_1^{<t-1>} + W_{x0}*a_0^{<t>} + b_{a1})$$

...

$$a_n^{<t>} = g_n(W_{an}*a_n^{<t-1>} + W_{xn}*a_{n-1}^{<t>} + b_{an})$$

...

$$\hat{y}^{<t>} = g_N(W_y*a_n^{<t>} + b_y)$$

where
$g_n$ denotes functions that could be different or the same,
$a_n^{<t>}$ denoted the activation data to be used for level n at time t+1
$W_{an}$ denotes the weights working on the activations from an earlier point in time,
$W_{xn}$ denotes the weights working on the activations from previous layer and
$W_{yn}$ denotes the weights working on the activations from the last layer. $\hat{y}^{<t>}$ is the output at time t and $b_{an}$ and $b_y$ are bias values.
The values in W and b are the ones being optimized.

When training the model, the weights W and the biases b are updated, typically after each step, that is, each rectangle in FIG. 5, but alternatively after a number of steps, or after the last step. The comparison of the estimated image to the input interior image is typically expressed as a penalty term in the cost function used when optimizing the parameters. This is based on the sum of the differences identified in each comparison as discussed in connection with step S32 above $$P_1 = \Sigma_{t=0}^T |G(Xt) - Yt|$$

Where the operator—indicates some sort of comparison, not necessarily a subtraction. The parameters are optimized to minimize this difference.

Another possible penalty term is based on the use of a classification function, D, which tries to discriminate between real images and generated images. This network may be optimized in conjunction with G. D is optimized to minimize the classification error of real and generated images. G is optimized to maximize this classification error.

It should be noted that the example model shown in FIG. 5 is only an example. As the skilled person is aware, there are several types of neural networks and any suitable one may be used according to the invention. A recurrent convolutional neural network (RCNN) is preferably used and a type of RCNN known as Long short-term memory (LSTM) is found to be particularly suitable for methods according to the invention.

The invention claimed is:

1. A computer-based method of training a deep learning model for providing an estimated image of an interior of a patient, based on a number of image sets, each image set comprising a first interior image of an interior of a person and a contour image of the person's outer contour at a specific point in time, and a second interior image of the interior of the person, comprising the steps of:
   a. submitting the image sets to a deep learning model; and
   b. training the model to establish an optimized parametrized conversion function G specifying the correlation between the interior of the person and the person's outer contour by, for each image set, applying the model to the contour image and the second interior image of the image set, comparing the output to the first interior image of the image set and using the result of the comparison to train the model.

2. A computer-based method according to claim 1, wherein the training step comprises:
   obtaining an initial parametrized conversion function G arranged to convert a contour image into an estimated image of the interior of the patient based on a first image set of the number of image sets;
   obtaining a first estimated interior image by applying the parametrized conversion function G to the contour image and the second interior image of the first image set;
   comparing, in a first comparing step, the first estimated interior image to the interior image of the first image set; and
   adjusting the initial parametrized conversion function G based on the comparison, to form a first parametrized conversion function G1, which is applied to the second image set.

3. A computer-based method according to claim 2, wherein the training step further comprises:
   applying the first parametrized conversion function G1 to the contour image of the second image set to obtain a second estimated image;
   comparing the second estimated image to the interior image of the second image pair, and adjust the initial parametrized conversion function G to form a second parametrized conversion function G2.

4. A computer-based method according to claim 2, wherein the training step further comprises:
   obtaining a second estimated interior image by applying the parametrized conversion function G to the contour image of the second image set;
   comparing, in a second comparing step, the second estimated interior image to the interior image of the second image pair;
   and adjusting the initial parametrized conversion function G based on the first and the second comparing step, to form a first parametrized conversion function G1.

5. A method according to claim 1, wherein the first and second interior images of each image set are segmentation maps and the model is trained to output a segmentation map.

6. A method according to claim 1, wherein the first second interior images of each image set are CT images and the model is trained to output a synthetic CT image.

7. A method according to claim 1, wherein each image set further comprises at least one slice of an MR image to provide additional information about the patient's interior.

8. A method according to claim 1, wherein the first interior image and the contour image of each image set are 4D images and the model is trained to output a synthetic 4D image.

9. A computer-based method of providing an estimated image of the an interior of a patient at a first point in time, comprising:
  a. providing an interior image of the interior of the patient at a second point in time, preceding the first point in time, to a deep learning model comprising an optimized parametrized conversion function based on the correlations between contours and interiors of persons;
  b. providing a contour image of the contour of the patient at the first point in time to the deep learning model; and
  c. outputting from the deep learning model an estimated image of the patient based on the interior image, the contour image and optimized parametrized conversion function G.

10. A method according to claim 9, wherein the contour image is based on data obtained from a surface scanning device.

11. A method according to claim 9, wherein the estimated image is a segmented image of the patient.

12. A method according to claim 9, wherein the estimated image is a CT image of the patient.

13. A method according to claim 9, wherein the steps b and c are repeated for several subsequent contour images to produce a set of estimated images constituting a 4D image.

14. A computer program product stored on a non-transitory medium which, when executed in a processor in a computer, is arranged to cause the computer to perform a method comprising:
  a. providing an interior image of an interior of the a patient at a second point in time, preceding a first point in time, to a deep learning model comprising an optimized parametrized conversion function based on the correlations between contours and interiors of persons;
  b. providing a contour image of the contour of the patient at the first point in time to the deep learning model; and
  c. outputting from the deep learning model an estimated image of the patient based on the interior image, the contour image and optimized parametrized conversion function G.

15. A computer system comprising a processor, and a program memory, said program memory comprising a computer program product according to claim 14.

* * * * *